United States Patent [19]
Gioia et al.

[11] 4,252,080
[45] Feb. 24, 1981

[54] ENCLOSED ENVIRONMENT FOR THE STUDY OF LIVING THINGS

[76] Inventors: Michael C. Gioia; Bruce M. Gioia, both of 128 Gordon St., Ridgefield Park, N.J. 07660

[21] Appl. No.: 105,384

[22] Filed: Dec. 19, 1979

[51] Int. Cl.³ .............................................. A01K 67/00
[52] U.S. Cl. ........................................... 119/1; 119/15
[58] Field of Search ................................ 119/1, 15, 17

[56] References Cited

U.S. PATENT DOCUMENTS

| | | | |
|---|---|---|---|
| 948,805 | 2/1910 | Akerlind | 119/1 |
| 3,626,902 | 12/1971 | Orfei | 119/15 |
| 3,874,335 | 4/1975 | Galasso | 119/1 |

*Primary Examiner*—Hugh R. Chamblee
*Attorney, Agent, or Firm*—Samuelson & Jacob

[57] ABSTRACT

Apparatus providing a transparent, enclosed environment for the observation and study of living things, the apparatus including an A-shaped enclosure with a selectively isolated media drawer at the base thereof and a transparent observatory mounted upon the enclosure for selective isolation of the interior of the observatory from the interior of the A-shaped enclosure.

14 Claims, 8 Drawing Figures

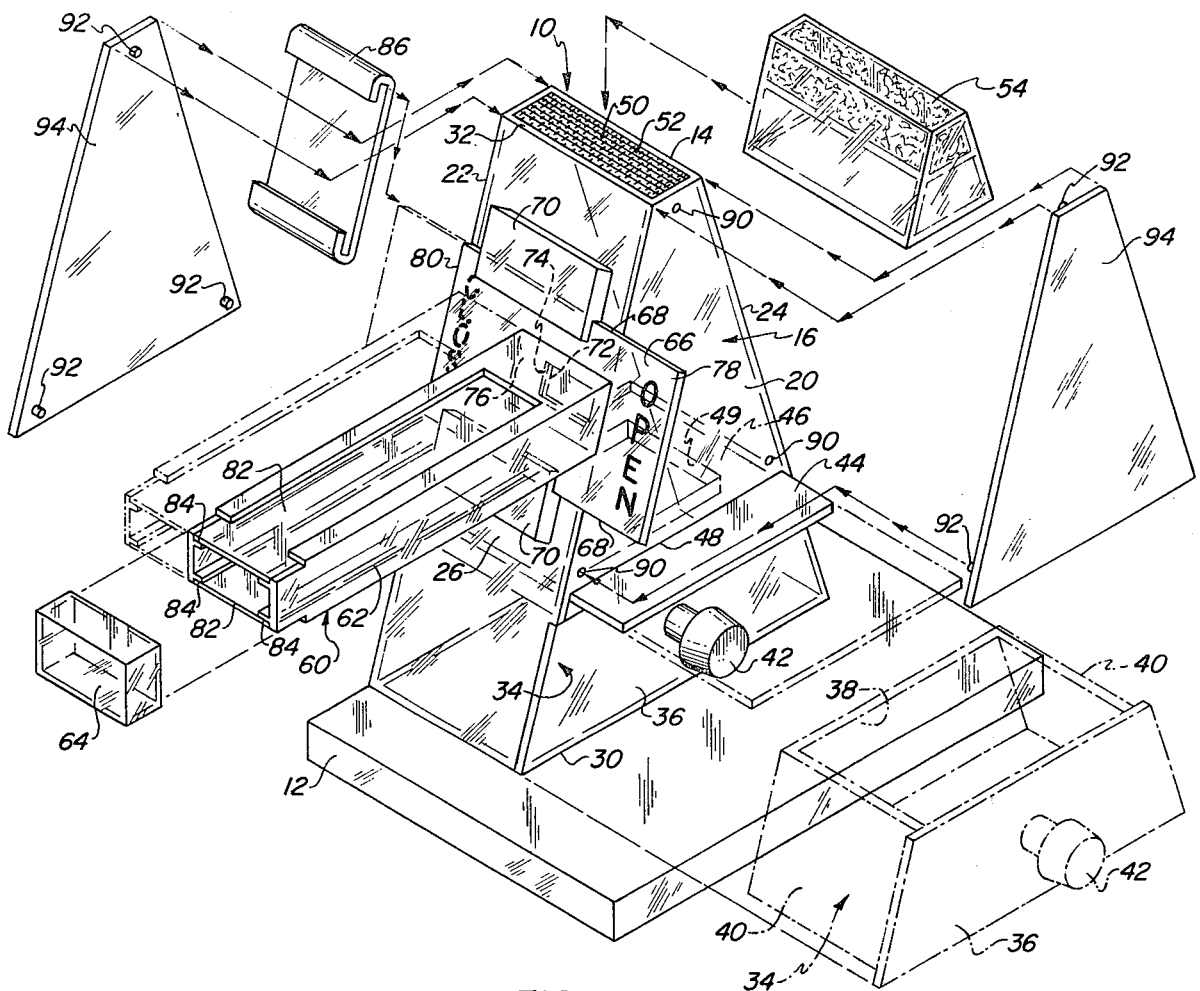

ENCLOSED ENVIRONMENT FOR THE STUDY OF LIVING THINGS

The present invention relates to apparatus for the observation and study of living things and pertains, more specifically, to apparatus for providing an enclosed environment for raising, observing and studying insects, such as fruit flies.

Geneticists and students of biology and genetics often raise, observe and study insects, and especially multiple generations of insects, in connection with investigations into conditions which influence biological changes in these insects. Among the most popular of these insects is the common fruit fly (*Drosophla Melangaster*) used by many investigators, both professional and amateur, for observation and study.

The most commonly available container for housing experimental insects in the past has been the one-pint glass milk bottle. The widespread availability of such a container, coupled with its ready use and ease of cleaning has made the container a favored device for raising fruit flies. Unfortunately, however, there are several drawbacks in the use of a bottle for raising fruit flies. The bottle is readily tipped over and easily broken. If not broken, a tipped bottle can lead to dislodgement of the culture media within the bottle, thereby disturbing the entire experiment. The thickness and curvature of the bottle wall interferes with optimal analytic observation and does not enable undistorted photography. The coupling of experimental apparatus to the bottle is not easily available. Further, in order to obtain multiple egg-bearing media from a single set or group of parent flies, it is necessary to anesthetize and transfer the parents from one bottle to another, thereby disturbing the parent flies and exposing the media to potential dislodgement.

It is an object of the present invention to provide apparatus which establishes an enclosed environment for living things, such as fruit flies, enabling greater ease of observation and study, as well as facilitating the raising of the observed living things.

Another object of the invention is to provide apparatus of the type described and having a configuration which lends stability to the structure so as to facilitate the intended use of the structure without mishap.

Still another object of the invention is to provide apparatus of the type described and having a configuration which lends itself to increased ease of observation and ready use of photographic techniques.

Yet another object of the invention is to provide apparatus of the type described and enabling increased ease in raising multiple generations of insects, such as fruit flies, as well as obtaining multiple egg-bearing media from a single set or group of parent flies, without requiring transfer of the flies themselves.

A further object of the invention is to provide apparatus of the type described and which facilitates a wide variety of experimental investigations.

A still further object of the invention is to provide apparatus of the type described and which is economically constructed of relatively inexpensive materials so as to be available readily for use by home hobbyists, as well as in the classroom and the research laboratory.

The above objects, as well as still further objects and advantages, are attained by the present invention which may be described briefly as apparatus for providing an enclosed environment for living things, such as insects, for observation and study, the apparatus comprising: a base; a top spaced upwardly from the base; an observation chamber having a basal area and an apical area, the basal area being substantially greater than the apical area, the chamber including a first pair of opposite walls extending upwardly from the base toward the top and establishing a front and a back for the chamber; a second pair of opposite walls extending upwardly from the base toward the top and establishing sides for the chamber; the walls of at least one of the first and second pairs of opposite walls converging toward one another from the base toward the top to render the basal area substantially greater than the apical area and to establish a generally A-shaped configuration; at least a portion of the walls of the chamber being transparent to enable the interior of the chamber to be viewed from the exterior; a media drawer removably received within the walls adjacent the base, the walls including wall portions surrounding the drawer, and the drawer having a peripheral configuration complementary to the configuration of the surrounding wall portions; and first isolation means received within the chamber adjacent the drawer for selectively isolating the interior of the chamber from the interior of the drawer to enable removal of the drawer while maintaining the chamber sealed.

The present invention will be more fully understood, while still further objects and advantages thereof will become apparent, in the following detailed description of a preferred embodiment illustrated in the accompanying drawing, in which:

FIG. 1 is a partially exploded perspective view illustrating an apparatus constructed in accordance with the invention;

FIG. 2 is a side elevational view of the apparatus;

FIG. 3 is a partial cross-sectional view taken along line 3—3 of FIG. 2.

FIG. 8 is a fragmentary view of a portion of FIG. 2 with component parts shown in another selected position.

Figures 4, 5, 6, 7:
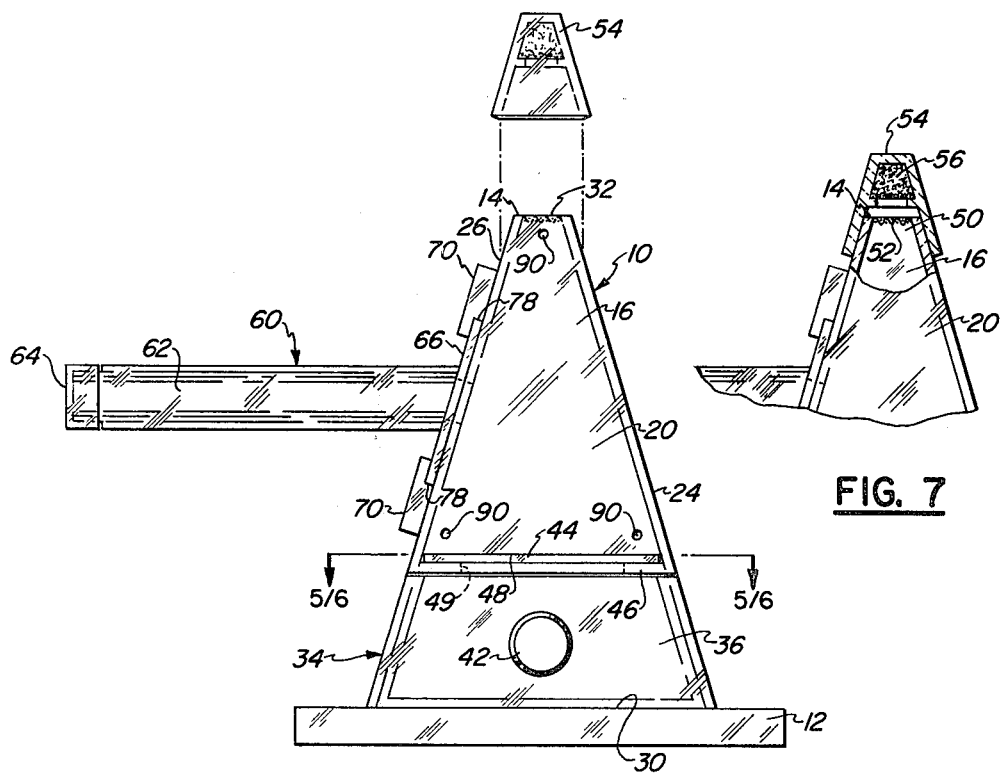
FIG. 4 is a front elevational view of the apparatus.
FIG. 5 is a top plan view of the apparatus, sectioned at line 5—5 of FIG. 4.
FIG. 6 is a view similar to FIG. 5, but with a component part in another selected position.
FIG. 7 is a fragmentary view of a portion of FIG. 4, with a component part in another selected location.

Referring now to the drawing, and especially to FIG. 1 thereof, an apparatus constructed in accordance with the invention is illustrated at 10. Apparatus 10 is constructed so as to provide an enclosed environment for raising, observing and studying fruit flies. Apparatus 10 includes a base 12 and a top 14 spaced upwardly from the base 12. An observation chamber 16 is established by a first pair of opposite walls, including a front wall 20 and a back wall 22, and a second pair of opposite walls, including right side wall 24 and left side wall 26.

Front wall 20 and back wall 22 are generally planar and extend upwardly from base 12 generally parallel to one another. Side walls 24 and 26 also are generally planar, but converge toward one another in the upward direction so as to establish a generally A-shaped configuration, with base 12 at the bottom of the A-shape, and top 14 at the apex.

Preferably, the basal area 30 is at least four times greater than the apical area 32 so that the chamber 16 is exceptionally stable and will resist toppling. Added resistance to tipping is provided by the enlarged, relatively heavy base 12.

In addition to the high degree of stability, the A-shaped configuration enables the provision of a relatively large media area with a relatively small volume available for the dispersal of the flies in the chamber 16. The small volume chamber facilitates observation of the flies, while the media area accommodates a larger number of eggs, as well as a good supply of food. The media is contained within a media drawer 34 received within the walls of the chamber 16 adjacent base 12. As best seen in FIGS. 2 through 6, as well as in FIG. 1, media drawer 34 has a drawer face 36 and a rear wall 38 complementary to the front and rear walls of the chamber 16, and sides 40 converging inwardly and upwardly to complement the angled side walls of the chamber 16. The converging sides 40 of drawer 34 aid in retaining media within the drawer such that the media is not dislodged readily. Media drawer 34 is selectively removable from the chamber 16, as illustrated in phantom in FIG. 1, with a drawer pull 42 being furnished for ease of manipulating the drawer 34.

In order to enable selective isolation of the media in the drawer 34 from the interior of chamber 16, a sliding plate 44 is received in chamber 16, just above the media drawer 34. Sliding plate 44 is supported upon a frame 46 which is located immediately above the drawer 34. A slot 48 in the front wall 20 enables sliding plate 44 to be moved inwardly selectively to cover the opening 49 in frame 46, as seen in FIG. 5, and thus isolate the interior of chamber 16 from the media in media drawer 34. Sliding plate 44 is selectively withdrawn, as seen in FIG. 6, to open the communication between the interior of chamber 16 and the media (not shown) in media drawer 34. Thus, with the sliding plate 44 withdrawn, as seen in FIG. 6, the flies in the chamber 16 have access to the media in the media drawer 34. However, should it be desired to remove the media, sliding plate 44 is pushed into place to isolate the flies from the media, as illustrated in FIG. 5, and the media drawer 34 can be removed without disturbing the flies. In this manner, the media can be replaced with fresh media at anytime, or another media can be placed within the environment. It becomes possible, then, to obtain multiple egg-bearing media from one group of parent flies without the need to transfer the flies from the chamber 16. The media drawer 34 provides a useful tool for dividing the media area for experimental food and chemical investigations. Temperature and pH readings are obtained readily with media-implanted devices. In addition, samples of larva or pupa may be taken without upsetting the remaining material.

Preferably, the walls of the chamber are constructed of a transparent material, such as a transparent synthetic resin. The planar walls provide flat surfaces which enable excellent views of the living habits of the insects within the chamber 16. In particular, the flat front and back walls 20 and 22 provide ease in using photographic apparatus and facilitate stereo-microscopic observation. Inexpensive materials may be used in the construction of chamber 16, thus rendering apparatus 10 relatively inexpensive and available for use by home hobbyists use well as in classroom and laboratory use. Such materials are so inexpensive as to enable the apparatus 10 to be disposable, rendering the apparatus useful in contamination studies where cleaning for reuse would not be practical.

Turning now to FIG. 7, as well as to FIGS. 1 and 4, ventilation is provided by means of a vent 50 located at the apex of the chamber 16. A fine mesh screen 52 is placed in the vent 50 to preclude escape of even the smallest insects. When it is desired to anesthetize the insects for transfer, or for any other reason, a cap 54 is placed over vent 50. Cap 54 contains a bed 56 of cotton which can be soaked with ether, or a like anesthetic, so that the anesthetic will enter chamber 16 and anesthetize the insects.

Referring to FIGS. 1 through 3 and 8, an additional observation tool is provided in the form of an isolation observatory 60 attached to left side wall 26. Isolation observatory 60 includes an elongate housing 62 with a removable cap 64 at one end and an integral flange 66 at the other end. The flange 66 has upper and lower edges 68 which are received between upper and lower guides 70 to secure the housing 62 to left side wall 26. A port 72 in the left side wall 26 communicates with an opening 74 in the flange 66 when the housing 62 is in a first position, as illustrated in full lines in FIG. 1, and in FIG. 2. In this first position of the housing 62, flies within the chamber 16 can enter the housing 62 for closer observation, the flies being encouraged by a light source (not shown) to enter the housing 62. Once the flies are in the isolation observatory 60, the entire assembly is shifted to a second position, as shown in phantom in FIG. 1, and in full lines in FIG. 8, to close off opening 74 by means of the partition provided by a portion 76 of side wall 26. In the first position, a first tab 78 projects beyond the front wall 20 to indicate that the isolation observatory 60 is in open communication with the chamber 16. In the second position, a second tab 80 projects beyond the back wall 22 to indicate that the isolation observatory is closed to the chamber 16.

The housing 62 includes planar observation plates 82 which may be fabricated of glass or a transparent synthetic resin material to provide flat surfaces for ease of observation and which are placed relatively close together to confine the flies to a relatively small space and thus facilitate observation. The observation plates 82 are easily removed and replaced by detaching the cap 64 and then sliding the plates 82 from the channels 84 within which the plates 82 are slidably retained. Thus, plates 82 may be replaced and can be exchanged for color filters for various experimental and photographic techniques. The flies in the isolation observatory 60 may be subjected to a variety of experiments, including exposure to X-ray, ultraviolet and other electromagnetic radiation.

The entire isolation observatory 60 is selectively removable from the chamber 16 either for closer observation of the flies or for transfer of the flies to another chamber. In such an instance, a cover plate 86 (see FIG. 1) is slipped over flange 66 to close opening 74 and confine the flies within the housing 62.

As an additional feature, front and back walls 20 and 22 each are provided with very small sockets 90. These sockets 90 are arranged to receive complementary pins 92 located on auxiliary plates 94. Auxiliary plates 94 are selected from a variety of filters or opaque materials which can be attached to either of the front and back walls 20 and 22 for photographic purposes or for different experimental techniques.

It is to be understood that the above detailed description of an embodiment of the invention is provided by way of example only. Various details of design and construction may be modified without departing from the true spirit and scope of the invention as set forth in the appended claims.

The embodiments of the invention in which an exclusive property or privilege is claimed are defined as follows:

1. Apparatus for providing an enclosed environment for living things, such as insects, for observation and study, said apparatus comprising:
   a base;
   a top spaced upwardly from the base;
   an observation chamber having a basal area and an apical area, the basal area being substantially greater than the apical area, the chamber including
   a first pair of opposite walls extending upwardly from the base toward the top and establishing a front and a back for said chamber;
   a second pair of opposite walls extending upwardly from the base toward the top and establishing sides for said chamber;
   the walls of at least one of said first and second pairs of opposite walls converging toward one another from the base toward the top to render the basal area substantially greater than the apical area and to establish a generally A-shaped configuration;
   at least a portion of the walls of the chamber being transparent to enable the interior of the chamber to be viewed from the exterior;
   a media drawer removably received within the walls, adjacent the base, the walls including wall portions surrounding the drawer, and the drawer having a peripheral configuration complementary to the configuration of the surrounding wall portions; and
   first isolation means received within the chamber adjacent the drawer for selectively isolating the interior of the chamber from the interior of the drawer to enable removal of the drawer while maintaining the chamber sealed.

2. The invention of claim 1 wherein one of said first and second pairs of walls converge and the other of said first and second pairs of walls essentially are parallel to one another such that the A-shaped configuration is in two dimensions only.

3. The invention of claim 1 or 2 wherein at least one of the walls includes a flat, planar surface coincident with a transparent portion to facilitate observation through the transparent portion.

4. The invention of claim 1 or 2 wherein the basal area is at least about four times greater than the apical area.

5. The invention of claim 1 wherein the first isolation means includes a plate mounted for sliding movement immediately above the media drawer.

6. The invention of claim 1 or 5 wherein the media drawer includes a front face, a rear wall and opposite sides extending between the front face and rear wall, the opposite sides converging upwardly, similar to the converging walls of the observation chamber.

7. The invention of claim 6 wherein the media drawer is mounted between the pair of converging walls of the observation chamber for sliding movement in directions perpendicular to the front face of the media drawer.

8. The invention of claim 1 including an isolation observatory attached to one of the walls, said isolation observatory including:
   an elongate housing extending between opposite ends;
   an opening at one of the opposite ends;
   a port in said one of the walls;
   mounting means mounting the elongate housing upon the apparatus such that the opening may be placed in registration with the port; and
   second isolation means for selectively isolating the interior of the housing from the interior of the observation chamber;
   the housing including transparent means enabling observation of the interior of the housing.

9. The invention of claim 8 wherein:
   the mounting means mounts the housing for selective movement between a first position and a second position on the apparatus, the opening being in registration with the port when the housing is in the first position; and
   the second isolation means includes a partition in registration with the port when the housing is in the second position to close the port.

10. The invention of claim 9 wherein the partition is a portion of one of the walls of the chamber.

11. The invention of claim 8 wherein the transparent means includes at least one transparent plate mounted in the housing for selective removal and replacement.

12. The invention of claim 8 wherein the transparent means includes a pair of transparent plates located in opposite wall portions of the housing, the pair of transparent plates being spaced apart a relatively short distance to enable confinement of the observed insects to a readily-observed small space.

13. The invention of claim 12 wherein at least one of the transparent plates is mounted in the housing for selective removal and replacement.

14. The invention of claim 11 or 13 wherein the one transparent plate includes planar surfaces for ease of observation therethrough.

* * * * *